US008007646B2

(12) United States Patent
Edwards et al.

(10) Patent No.: US 8,007,646 B2
(45) Date of Patent: *Aug. 30, 2011

(54) FLUORESCENT DETECTION OF PROTEINS IN POLYACRYLAMIDE GELS

(75) Inventors: Robert A. Edwards, Calgary (CA); Raymond J. Turner, Calgary (CA); Carol Ladner, Calgary (CA); Jean Starkey, Bozeman, MT (US); Eric Larson, Bozeman, MT (US); Dmitri Kazmin, Durham, NC (US)

(73) Assignees: Univeristy Technologies International Inc., Calgary (CA); Montana State University, Bozeman, MT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/505,859

(22) Filed: Jul. 20, 2009

(65) Prior Publication Data

US 2010/0089753 A1    Apr. 15, 2010

Related U.S. Application Data

(63) Continuation of application No. 10/248,526, filed on Jan. 27, 2003, now Pat. No. 7,569,130.

(60) Provisional application No. 60/319,099, filed on Jan. 25, 2002, provisional application No. 60/352,225, filed on Jan. 29, 2002, provisional application No. 60/319,810, filed on Dec. 24, 2002.

(51) Int. Cl.
*G01N 27/453* (2006.01)

(52) U.S. Cl. .................. 204/456; 204/466; 204/470

(58) Field of Classification Search .......... 204/600–621, 204/450–470
See application file for complete search history.

(56) References Cited

U.S. PATENT DOCUMENTS

| 4,119,521 A | 10/1978 | Chirikjian | 204/469 |
| 5,865,975 A | 2/1999 | Bishop | 204/618 |
| 7,569,130 B2 * | 8/2009 | Edwards et al. | 204/459 |

OTHER PUBLICATIONS

"SPYRO Orange and Red protein gel stains," brochure from Amersham Biosciences, 4 pages, 2000.
Berggren et al., "Background-free, high sensitivity staining of proteins in one- and two-dimensional sodium dodecyl sulfate-polyacrylamide gels, etc.," *Electrophoresis*, 21:2509-2521, 2000.

(Continued)

*Primary Examiner* — Alex Noguerola
(74) *Attorney, Agent, or Firm* — Fulbright & Jaworski (57) ABSTRACT

The mechanism of the UV light-induced reaction between the indole moiety of tryptophan and chloroform, and the structure of the modified tryptophan and polypeptides including such modified tryptophan residues. The excited indole moiety, which is formed upon UV light irradiation, emits a solvated electron which initiates a series of events that yield fluorescent derivatives that have CHO group covalently bound to the indole moiety. These derivatives are herein referred to as formyltryptophan, and are relatively stable. Similar reactions are observed when 5-hydroxytryptophan, 5-fluorotryptophan, or N-methylindolacetate are used in place of tryptophan, or when other haloalkanes, such as trichloracetic acid, trichlorethanol, trichlorethane, bromoform, and iodoactetate are used in place of chloroform. The derivatives can be used in a variety of applications in fluorescence spectroscopy, and for nuclear magnetic resonance, X-ray crystallography, infra-red spectroscopy, circular dicroism and mass spectroscopy. Additionally, the UV light-induced reaction between the indole moiety of tryptophan and haloalkanes can be used to prepare derivatives of tryptophan for chemical cross-linking studies of proteins and peptides.

10 Claims, 8 Drawing Sheets

OTHER PUBLICATIONS

Edwards et al., "The light-induced reactions of tryptophan with halocompounds," *Photochemistry and Photobiology*, 75:362-368, 2002.

Edwards et al., "Visualization of proteins in acrylamide gels using ultraviolet illumination," *Analytical Biochemistry*, 301:91-96, 2002.

Koutny et al., "On-line detection of proteins in gel electrophoresis by ultraviolet absorption and by native fluorescence utilizing a change-coupled device imaging system," *Anal. Chem.*, 65:183-187, 1993.

Leibowitz et al., "Visualization and elution of unstained proteins from polyacrylamide gels," *Analytical Biochem.*, 137:161-163, 1984.

Mehl, "Separation and characterization of myelin proteins," *Advances in Experimental Medicine and Biology*, 32:157-170, 1972.

Office Action, issued in U.S. Appl. No. 10/248,526, date mailed—Nov. 18, 2005.

Office Action, issued in U.S. Appl. No. 10/248,526, date mailed—Mar. 30, 2006.

Office Action, issued in U.S. Appl. No. 10/248,526, date mailed—Sep. 5, 2006.

Office Action, issued in U.S. Appl. No. 10/248,526, date mailed—Mar. 26, 2007.

Office Action, issued in U.S. Appl. No. 10/248,526, date mailed—May 23, 2008.

Office Action, issued in U.S. Appl. No. 10/248,526, date mailed—Feb. 19, 2009.

Patton, "A thousand points of light: the application of fluorescence detection technologies to two-dimensional gel electrophoresis and proteomics," *Electrophoresis*, 21:1123-1144, 2000.

Pinchuk et al., "Spectral characteristics and mechanisms of forming 'choloroform dependent' tryptophan photoproducts," *Institute of Photobiology*, 59:312-317, 1993.

Privat and Charlier, "Photchemical modifications of the tryptophan residues of wheat-germ agglutinin in the presence of trichloroethanol," *Eur. J. Biochem.*, 84:79-85, 1978.

Roegener et al., "Ultrasensitive detection of unstained proteins in acrylamide gels by native UV fluorescence," *Analytical Chem.*, 75:157-159, 2003.

Vorpel et al., "Chloroform-dependent photoproducts of tryptophan," *Biophysics*, 37:743-745, 1992.

Wong et al., "Heating greatly speeds coomassie blue staining and destaining," *BioTechniques*, 28:426-432, 2000.

Yamamoto et al., "Ultraviolet imaging densitometry of unstained gels for two-dimensional electrophoresis," *Analytical Biochemistry*, 191:58-64, 1990.

\* cited by examiner

FLUORESCENT DETECTION OF PROTEINS IN POLYACRYLAMIDE GELS

CROSS REFERENCE TO RELATED APPLICATIONS

This application is a continuation of U.S. patent application Ser. No. 10/248,526 filed on Jan. 27, 2003, now U.S. Pat. No. 7,569,130; which claims the priority benefit of U.S. Provisional Patent Application No. 60/319,099 filed Jan. 25, 2002; No. 60/352,225 filed Jan. 29, 2002; and No. 60/319,810 filed Dec. 24, 2002; the contents of each of which are incorporated by reference.

BACKGROUND OF INVENTION

This invention relates to polyacrylamide gel electrophoresis and in particular, to a method of visualizing proteins in a polyacrylamide gel.

Polyacrylamide gel electrophoresis is a well-known technique for determining the molecular weight of a protein and for separating proteins on the basis of their molecular weight. Electrophoresis in the absence of any denaturing reagent (native-PAGE) results in separation on the basis of charge and size. It gives an estimation of the size of the folded protein by reference to proteins of known size. In order to determine the molecular weight of the polypeptide chain it is necessary to carry out the electrophoresis in the presence of the anionic detergent sodium dodecyl sulphate (SDS-PAGE). This detergent not only completely unfolds the protein but interacts with the unfolded chain such as to give a constant charge density. This means that separation is only based upon molecular weight. Calibration of the gel with marker proteins of known molecular weight allows estimation of the molecular weight of unknown proteins.

Visualization of the proteins separated by SDS-PAGE is typically carried out by staining the gel with Coomassie brilliant blue or Amido black dyes. Other non-specific visualization techniques include silver precipitation or staining with fluorescent compounds. Coomassie blue staining is the most common technique and, similar to other prior art techniques, typically involves several hours of protein fixation, staining and destaining. There have been many attempts to provide shorter staining protocols.

The use of fluorescence for protein detection is of course well established in biochemistry. Preelectrophoretic labeling of proteins with UV-excitable fluorophores, such as FITC (flourescein isothiocyanate) or bromobimane compounds (1) followed by postelectrophoretic visualization under UV light has been successfully used for many years. Also, several methods have been developed for postelectrophoretic fluorescent labeling with stains such as 1-aniline-8-naphthalene sulfonate (2) and o-phthaladehyde (3). All these methods involve lengthy labeling steps and each of them has intrinsic limitations such as altered electrophoretic mobility on native PAGE in the case of preelectrophoretic labeling or low sensitivity in the case of postelectrophoretic staining (4). Recently two new fluorescent dyes, SYPRO red and SYPRO orange, have been introduced to detect proteins in SDSPAGE (5). Although quite sensitive, their use is expensive, somewhat time-consuming, and dependent on the presence of SDS.

There is still a need in the art for further improvements in fluorescent protein visualization.

SUMMARY OF INVENTION

It is known that a light driven reaction between chloroform and the indole moiety of tryptophan (Trp) yields products that emit at long wavelengths. This generation of blue fluorescence in biological tissue samples is used to monitor aging and lipid peroxidation; but the use of chloroform/methanol in the extraction of tissues and subsequent production of long wavelength emitting substances upon irradiation has been noted as a complication in these studies.

The applicants have recently determined that a UV-light-dependent reaction between Trp in the presence of trichloro compounds such as trichloroacetic acid yields fluorescent products that emit in the visible spectrum. This reaction is similar to the reaction between Trp and chloroform described in the prior art. This knowledge permitted the development of a procedure for visualizing proteins after SDS-PAGE which allowed fluorescent visualization of proteins shortly after completion of electrophoresis and without laborious labeling or staining steps.

In one aspect, the invention may comprise a method of visualizing a protein in a polyacrylamide gel, comprising the steps of:
(a) incorporating a haloalkane into the gel, either pre- or post-electrophoresis, which haloalkane reacts with tryptophan residues in the proteins to form fluorescent compounds when illuminated with ultraviolet light; and
(b) electrophoretically migrating the protein in the gel; and
(c) illuminating the gel with ultraviolet light; and
(d) detecting the fluorescence of the formed compounds.

Preferably, the haloalkane is a trichloroalkane and more preferably, the trichloroalkane is selected from the group consisting of chloroform, trichloroacetic acid and trichloroethanol, or mixtures thereof. In one embodiment, the haloalkane is incorporated into the gel by soaking the gel (post-electrophoresis) in a haloalkane solution. In another embodiment, the haloalkane is incorporated into the gel pre-electrophoresis before polymerization of the gel. In another embodiment, the haloalkane may be incorporated into the buffer in which the proteins are dissolved pre-electrophoresis.

In another aspect, the invention may comprise a polyacrylamide gel for electrophoretically separating proteins by molecular weight, the gel comprising a haloalkane which reacts with tryptophan residues in the proteins to form compounds which fluoresce when subjected to ultraviolet light.

In another aspect, the invention may comprise a kit for forming a polyacrylamide gel for electrophoretically separating proteins by molecular weight, comprising a haloalkane for incorporation into the gel which reacts with tryptophan residues in the proteins to form compounds which fluoresce when subjected to ultraviolet light.

BRIEF DESCRIPTION OF DRAWINGS

FIG. 3 shows gels visualized under different conditions to determine optimum sensitivity. Bio-Rad low-molecular-weight standards at 1.2, 3.0, and 6.0 µg per lane (which corresponds to 0.2, 0.5, and 1.0 µg per band) were run on thin (0.75 mm thick) 12% polyacrylamide gels. After electrophoresis portions of gels A and B were soaked in 5% TCA, 10% TCA, 20% TCA, or 50% methanol:water saturated with chloroform for 10 min, washed with water at least five times over a 10-min period, and then illuminated for 5 min on the transilluminator. Gel C has been CBB Stained after treatment with saturated chloroform as described above for gel B. Pictures were taken with a transilluminator digital camera using a 4-s integration time.

FIG. 5 shows fluorescence monitoring of the reaction of Trp in the presence of TCA. Emission spectra of 10 mM Trp in the presence of 100 mM TCA with 280-nm excitation spectra. Scans were begun at 0, 2, 4, 6, 10, 14, and 18 min. The inset shows the excitation spectra with 450-nm emission that was obtained after the scanning.

FIG. 6 shows fluorescence monitoring of the reaction of Trp and n-acetyl-L-tryptophanamide (NAWA) in the presence of HCl. Emission spectra of 10 mM Trp plus 100 mM HCl with 280-nm excitation spectra. Scans were begun at 0, 10, and 18 min. The line near zero is for 10 mM NAWA plus 100 mM HCl at the 18-min scan and is also magnified 10-fold (designated 103) for clarity.

FIG. 7 shows a comparison between trichloroethanol (TCE) added pre-electrophoresis in gel visualization and Coomassie Brilliant Blue (CBB) staining.

FIG. 8 is a graph showing the relationship between TCE concentration and fluorescent intensity. The data was obtained from a SDS-PAGE gel of low molecular weight standards conducted with various percentages (vol/vol) of TCE in the gel before electrophoresis. Intensities per µg are from the sum of intensities from phosphorylase b, albumin, ovalbumin and trypsin protein bands. The error bars are the standard deviations.

FIG. 9 shows the linear dynamic range of the TCE in gel method and the effect of tryptophan content. Intensities are from a 12% SDS-PAGE with 0.5% (vol/vol) TCE in the gel.

DETAILED DESCRIPTION

The present invention provides for methods of visualizing proteins by means of an ultraviolet (UV) light dependent reaction between tryptophan (Trp) and a haloalkane, which results in product which fluoresce in the visible range. When describing the present invention, all terms not defined herein have their common art-recognized meanings.

The present invention comprises a method to rapidly visualize proteins in polyacrylamide gels following the fixation step in a standard staining procedure following electrophoresis. The method utilizes the fluorescence of products of the reaction between modified tryptophan residues present in the proteins and trichloro compounds, such as chloroform or TCA. Since TCA is commonly used as a general purpose fixative in staining protocols, this method effectively does not introduce any additional steps in the conventional CBB staining routine. In short time a researcher gets a first glimpse at the results of the electrophoresis run and is able to visualize the most abundant protein species. In many cases, this preview may be sufficient to answer most questions regarding the presence, relative abundance, mobility, and aggregation of well-represented proteins. Following the initial visualization, the gel can be further stained or blotted with traditional methods, thus avoiding spending extra "hands-on" time on fast "hot stainer and destainer" protocols, working with hot solvents and generating unpleasant odors. Generation of fluorescent protein bands involves a photochemical reaction between tryptophan residues within proteins and haloalkanes.

As used herein, the term "haloalkane" refers to aliphatic hydrocarbons substituted with at least one halogen atom. The hydrocarbons may include alcohols, acids and amides. Preferably, the haloalkane is a trihaloalkane including without limitation chloroform, bromoform, iodoform, 1,1,1-trihaloalkanes, 1,1,1-trihaloalkanols such as trichloroethanol, trichloroethanol, trichloroacetate and tribromoacetate. Haloalkanes may also include single and di-substituted haloalkanes such as iodoacetate. As used herein, "ultraviolet light" or "UV light" refers to electromagnetic radiation beyond the violet end of the visible spectrum. The wavelength of UV light may range from less than about 200 nm to about 400 nm. As used herein, to "fluoresce" means to emit light detectable by the naked eye or by an imaging system such as a film or digital camera.

In a basic embodiment, proteins in a polyacrylamide gel may be visualized by incorporating a haloalkane into the gel, which haloalkane reacts with tryptophan residues in the proteins to form compounds which fluoresce when illuminated with ultraviolet light. Thereafter, when the gel is illuminated with ultraviolet light, the fluorescent proteins may be detected by the naked eye or by using imaging devices. The haloalkane may be incorporated into the gel either pre-electrophoresis or post-electrophoresis.

Therefore, in one embodiment, after proteins have been electrophoretically resolved in a gel with a SDS-PAGE procedure, the gel may be soaked in a haloalkane solution and then illuminated with UV light to produce fluorescent protein bands. In another embodiment, the haloalkane may be added directly to the gel prior to electrophoresis. Preferably, the haloalkane may be added to the gel prior to polymerization. The applicants have found that this improvement may allow the speed and sensitivity of the method to be improved so that as little as 0.1 µg of typical globular proteins can be visualized very shortly after completion of electrophoresis, with minimal processing of the gel. For proteins having a high percentage of tryptophan, a method as described herein may detect as little as 0.01 µg of such proteins which is much more sensitive than Coomassie brilliant blue (CBB). The methods described herein may be particularly useful to detect integral membrane proteins which do not stain well with CBB. A comparison of TCA post-electrophoresis soak and CBB staining may be seen in FIG. 1.

The haloalkane may be (but is not limited to) trichloroethanol (TCE), trichloroacetic acid (TCA) or chloroform. Preferably, the haloalkane comprises TCE, alone or in combinations of TCE and TCA. TCE is most preferred as it is less volatile than chloroform and thus less likely to be inhaled. Furthermore, TCE is less corrosive than TCA.

Compared to SYPRO Ruby™, the most sensitive of the SYPRO™ series (6), the methods herein using TCE are less sensitive; however, it is much faster and far less expensive. Furthermore SYPRO Ruby™, touted as the best for 2-dimension electrophoresis, has a similar binding mechanism as CBB, so it can be expected that proteins not efficiently visualized with CBB will not be visualized by SYPRO Ruby™ either.

With post-electrophoretic embodiments, the gel may be soaked in a haloalkane solution varying from about 1% to about 30% haloalkane, preferably between about 5% to about 20% haloalkane, and most preferably about 10% haloalkane. In one embodiment, particularly good results may be obtained using 10% TCE in methanol:water (1:1) in the soaking procedure. The soaking step may vary from 1 minute to about 10 minutes, and preferably about 5 minutes in length. The variables of haloalkane concentration and the length of soaking time are not essential elements of the invention and may be varied to obtain optimal results in each particular case with simple experimentation.

Incorporating a haloalkane into the gel prior to electrophoresis has been found to provide slightly greater intensity and faster visualization, as a result of eliminating the soaking step referred to above. In comparison CBB methods take at least 30 minutes to stain and several, hours to destain. A comparison of the results may be seen in FIGS. 7A and 7B. The haloalkane may be added to the gel prior to polymerization in a suitable concentration which may vary from about 0.02% to about 2.0% (v:v) or more. The applicants have found that increasing TCE concentration in the gel tends to increase the band intensity up to about 0.5% TCE (v:v) after which the intensity no longer increases, as may be seen in FIG. 8. Again, the concentration of the haloalkane in the gel is not an essential element of the invention and may be varied to obtain optimal results with simple experimentation.

Figure 9A:
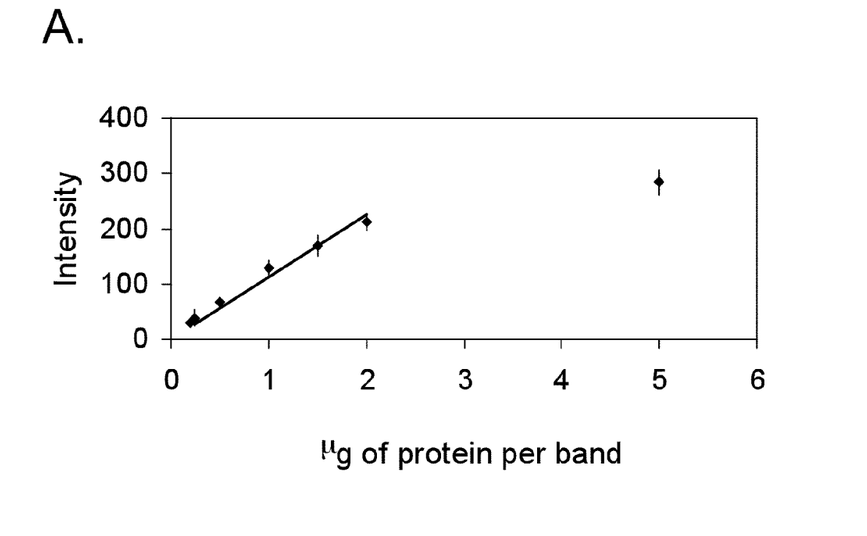
FIG. 9A shows the sum of intensities from phosphorylase b, albumin, ovalbumin and trypsin with 0.25, 0.5, 1.0, 1.5 µg per band were used.
Figures 9A, 9B:
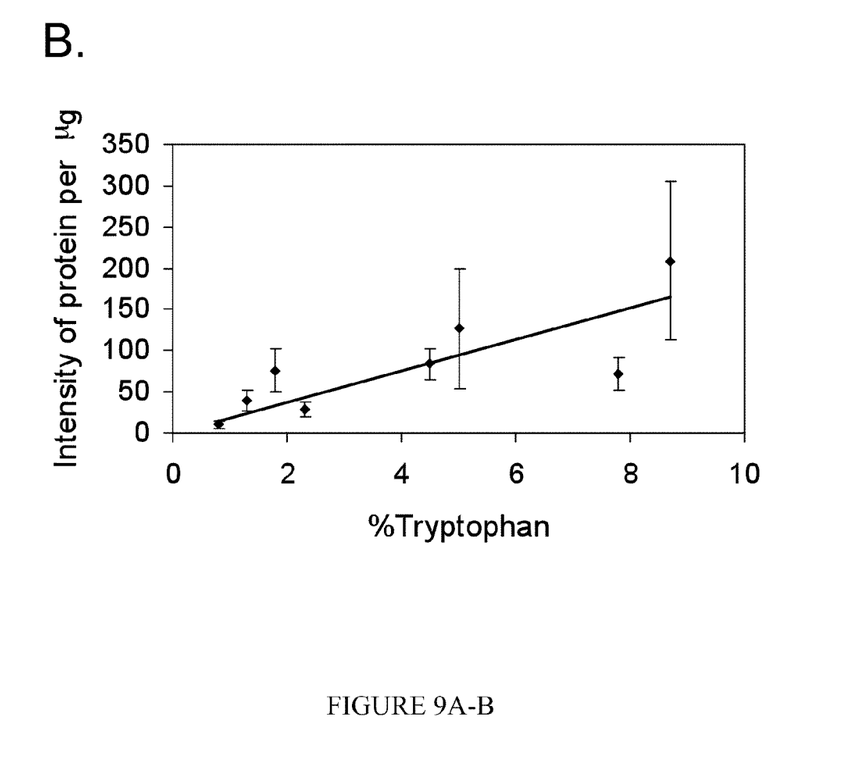
FIG. 9B shows the intensity per µg obtained from the serum albumin (0.8%), ovalbumin (1.3%), trypsin inhibitor (1.8%), phosphorylase b (2.3%), carbonic anhydrase (4.5%), EmrE (5.0%), lysozyme (7.8%), and DmsD (8.7%) using 0.25 and 0.5 µg of protein. The error bars are the standard deviations.

The pre-electrophoresis incorporation of a haloalkane method offers a linear dynamic range from 0.2 µg to 2 µg of protein with a correlation coefficient of 0.98 (see FIG. 9A). The sensitivity limit of the method for globular proteins with typical percentages of tryptophan (0.8 to 2.3%) is approximately 0.1 µg. All the proteins in low molecular weight standards are detectable at this limit. For carbonic anhydrase, which has a high tryptophan percentage (4.5%), the sensitivity limit is 0.01 µg. Testing the linear dynamic range for specific proteins with the TCE staining method demonstrates that the upper limit of the linear dynamic range is lower with proteins of higher tryptophan percentage. Thus the dynamic range is shifted to lower protein amounts, so both the upper limit and the sensitivity limit is lower.

Figure 3A:
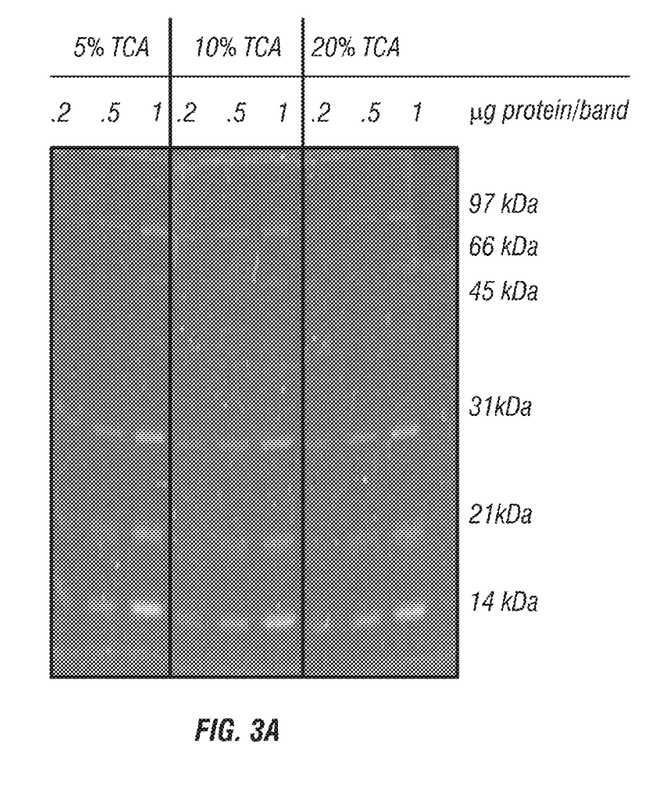
Figure 3B:
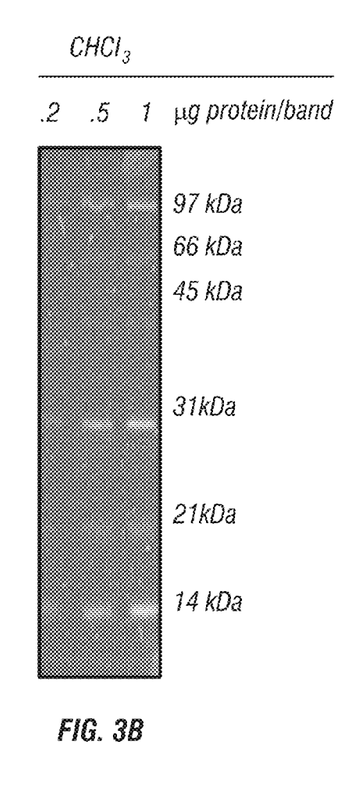

The intensity of protein bands increases as the percentage of tryptophan increases as shown in FIG. 3B. The intensity appears to increase to a maximum intensity and then level off. Phosphorylase b (2.3% Trp, 97 kDa) does not fit the pattern. A possible explanation for this is that phosphorylase b band is thin and once all the pixels are lit up in the small area an increase in intensity cannot be measured. Similar studies done using the method in which TCE was soaked into the gel after electrophoresis, resulted in wider phosphorylase b bands and consequently the intensity of the band fit the pattern better (results not shown). When fitting a linear line to the pattern (intercept set to zero) the correlation coefficient is 0.78, which is statistically significant using a 1 tailed t-test and a 95% confidence limit.

Figure 7A:
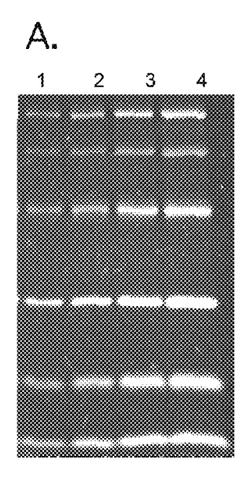
FIG. 7A shows the detection of low molecular weight standards with 0.5% TCE in 12% SDS-PAGE.
Figure 7B:
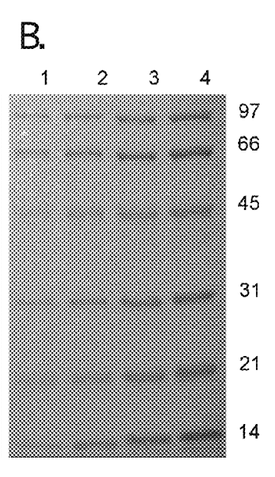
FIG. 7B shows a CBB stain of the gel from FIG. 7A.
Figure 7C:
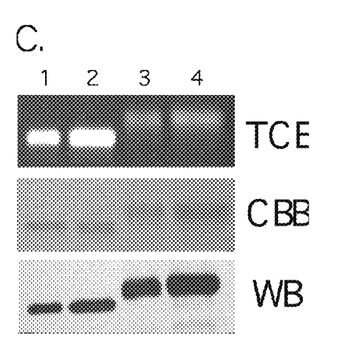
FIG. 7C shows an SDS-PAGE with 0.5% TCE of 0.25 µg and 0.5 µg DmsD:His6 (lane 1 and 2) and TehB:His6 (lane 3 and 4) visualized with UV light and then western blotted with antiHis6. A duplicate gel was stained with CBB.
Figure 7D:
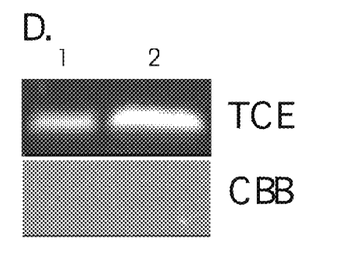
FIG. 7D shows a SDS-PAGE with 0.5% TCE (v:v) of 0.25 µg and 0.5 µg EmrE (lane 1 and 2) visualized in UV light and then stained with CBB.

The haloalkane reaction of tryptophans does not interfere with subsequent blotting of proteins from the gel using known blotting procedures. As shown in FIG. 7C, proteins bands which fluoresce under UV illumination may also be detected by a Western blot, subsequent to the fluorescent detection procedure.

Haloalkane-UV modified tryptophan protein detection has the potential to be especially beneficial for detection of integral membrane proteins. The membrane spanning regions of integral membrane proteins have a higher percentage of tryptophans then globular proteins (7, 8).

The modified tryptophan visualization of the present invention is useful because the speed of the visualization technique allows nearly immediate protein detection in PAGE. The methods of the present invention may be implemented in automated and high throughput technologies for proteomics. Visualization techniques in accordance with the present invention may complement other staining techniques to allow detection of proteins not stained efficiently by these methods.

Although the invention has been described in relation to SDS-PAGE, the methods described herein are applicable to non-denaturing gel electrophoresis.

EXAMPLES

The following examples of general methods and materials are intended to illustrate specific embodiments of the invention and not to limit the invention claimed below.

Example 1

Post-Electrophoresis Incorporation—Materials and Methods

Electrophoresis was performed in each case using an electrophoresis apparatus from Owl Scientific (Portsmouth, N.H.) with 15 3 20 3 0.15-cm gel cassettes or a Mini Protean II™ system from Bio-Rad (La Jolla, Calif.). Upon completion of electrophoresis, the gel was removed from the cassette and placed in the haloalkane solution. After soaking from 5 to 10 minutes, the haloalkane solution was decanted, and the gel was rinsed several times with tap water to remove residual solution and then placed in water to prevent drying. If trichloroacetic acid (TCA) is used, it is important to rinse the gel to remove excess TCA prior to protein visualization since TCA is corrosive and will damage the UV transilluminator. To visualize proteins, the gel was subjected to UV illumination using a standard UV box. During the course of UV irradiation, resolved proteins became visible as bluish-green bands against the background of pale blue gel matrix. Fluorescence develops gradually and the bands become fully visible after 1 to 5 min of UV exposure. Depending on the UV transilluminator used and the gel documentation system available, differences in the ability to photograph the results will exist. A Bio-Rad Gel Doc™ system and an UltraLum™ transilluminator (300-nm) or a mounted photographic camera with f5 2, 58-mm objective equipped with an orange UV filter proved suitable. Exposure times of 5 to 20 seconds worked best for the photographic images shown in this manuscript, using ASA 400 TMAX™ black and white film (Kodak). Illuminating the gel from the side or placing it on top of a UV box gave equivalent results for the purpose of visualization and photography. Fluorescence, once developed, is stable for several hours in room light and is immediately visible upon repetitive UV irradiation. Gels may be irradiated in the transilluminator for as long as 30 min without any noticeable loss of fluorescence. It is also possible to soak gels in water after TCA treatment for an extended period of time: we have allowed up to 1.5 min between removal of TCA and visualization under UV without any loss of sensitivity. Following visualization under UV, the gel can be stained using standard CBB protocol to visualize less abundant protein species.

All excitation and emission spectra were recorded with a Fluorolog-3™ (ISA Jobin-Yvon Spex) fluorometer using a 450-W Xe lamp with 5-nm slitwidths for both the excitation and the emission, while stirring in the 1.00-cm cuvette with a small bar at about two revolutions per second. Spectra were taken in a temperature controlled environment at 20° C. Because the light-dependent reaction is driven by the excitation light, repetitive scans were made at a uniform scan rate at 2-min intervals to follow the reaction.

Example 2

Comparison of Fluorescent Detection with CBB Staining

FIG. 1 shows results which validate the utility of this method. In FIGS. 1A and 1B, approximately 20 μg of a recombinant protein and three of its mutants, all with electrophoretic mobility corresponding to 46 kDa, were loaded on the gel in sample buffer either with or without added β-mercaptoethanol (BME). FIG. 1A is a picture of the gel soaked in 10% TCA for 5 minutes and rinsed three times with tap water. FIG. 1B is the same gel after conventional CBB staining. It is evident that wild-type (wt), as well as mutants 1 and 2, form aggregates of a higher molecular weight in the absence of BME, while mutant 3 does not. These proteins could be visualized by UV illumination 10 min after the completion of the PAGE run. In FIGS. 1C (TCA) and 1D (CBB), an expression of a recombinant protein by two bacterial clones and its purification were followed. The purifications were run in duplicate. The gel demonstrates that clone 1 does not express the target protein, while clone 2 does. The purified fraction contains the major band at approximately 45 kDa and a minor contaminant or degradation product at approximately 20 kDa. The bands on the gels were visible in less than 10 minutes.

Figure 2A:
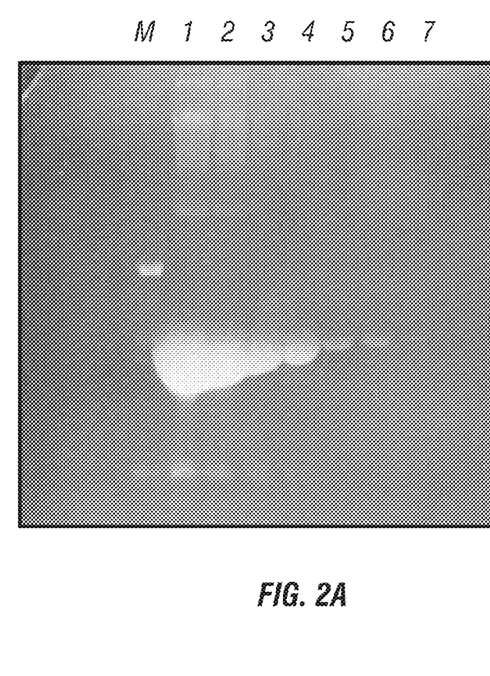
FIG. 2A shows a gel wherein bovine serum albumin (BSA) was loaded on the gel in the following amounts: Lane 1 250 µg, lane 2 125 µg, lane 3 50 µg, lane 4 25 µg, lane 5 5 µg, lane 6 2.5 µg, lane 7 0.5 µg. M, molecular weight markers. Protein was visualized by the TCA post-electrophoresis soak method.
Figure 2B:
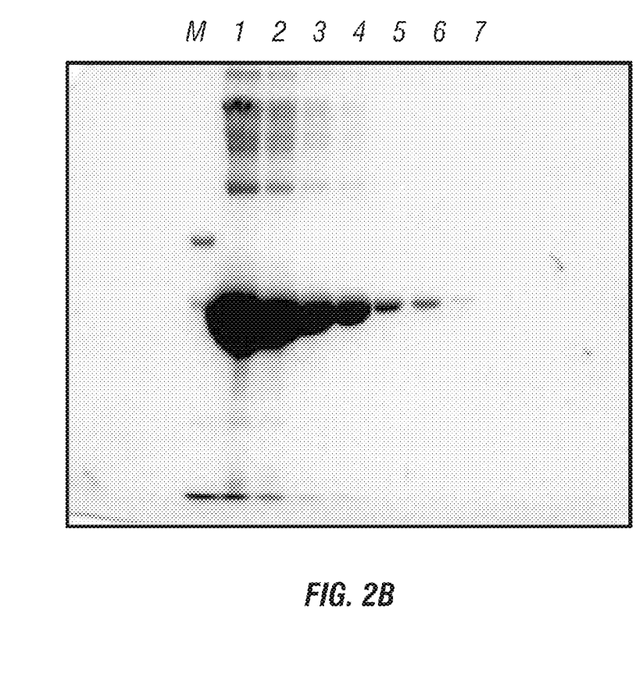
FIG. 2B shows the same gel stained overnight with CBB R-250 (B).

FIG. 2 demonstrates the sensitivity of this method using thick (1.5 mm) gels Bovine serum albumin (BSA) was loaded on the gel: Lane 1 250 μg, lane 2 125 μg, lane 3 50 μg, lane 4 25 μg, lane 5 5 μg, lane 6 2.5 μg, lane 7 0.5 μg. M, molecular weight markers. The gel was run and resolved BSA was visualized using the described TCA protocol. As little as 2.5 μg of BSA could be detected visually and as little as 0.5 μg of BSA could be detected photographically. The band in FIG. 2, lane 5 (5 μg BSA), was clearly visible, while the band in FIG. 2, lane 6 (2.5 μg BSA), was somewhat harder to see, although still distinguishable.

The band in FIG. 2, lane 7 (0.5 μg BSA), was not visible by the naked eye but was detectable by photography. It should be noted that black and white photography is in this case more sensitive than naked eye. The protein band in A, lane 7, is clearly visible on the photograph, but was indistinguishable by visual observation.

FIG. 3 illustrates trials run on thin gels (0.75 mm). The molecular weight standards used in FIG. 3 are the same standards used in FIG. 2. However, in FIG. 2 as much as 3 μg of protein per band of molecular weight markers were used to give the same intensity of bands as is shown in FIG. 3, whereas in FIG. 3 the maximum load was 1.0 μg per band. As well, three different TCA concentrations were used, as well as a chloroform solution. As may be seen in FIG. 3, we determined that TCA concentration can be decreased to 5% without loss of sensitivity and that chloroform can be used in place of TCA. In the window of the transilluminator, the bands on the gel soaked in chloroform and then illuminated are somewhat brighter than those treated with TCA, but the optics of the transilluminator give them about the same magnitude when photographed. While we had to use a mounted photographic camera to obtain images of thick (1.5 mm) gels, the protein bands on thin (0.75 mm) 12% polyacrylamide were sufficiently intense that they were recorded using a digital camera attached to the transilluminator. Comparison between FIGS. 2 and 3 suggests that the use of thinner gels, as well as more sophisticated documentation equipment appears to result in greater sensitivity.

Example 3

Fluorescence Caused by Reaction with Haloalkane

Figure 4A:
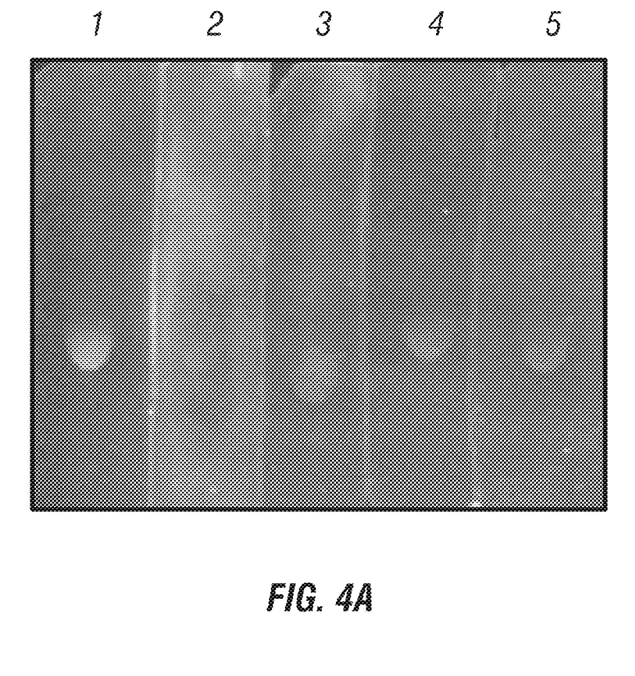
FIG. 4 shows that protein fluorescence is largely specific for TCA in contrast with other acids. BSA (0.1 µg/lane) was resolved on SDSPAGE, gel was cut in strips, and each strip was soaked in 20% aqueous solution of an acid as indicated below. Strips were photographed in UV light (A) and then stained overnight with CBB R-250 (B). Lane 1, TCA; lane 2, acetic acid; lane 3, hydrochloric acid; lane 4, sulfuric acid; lane 5, nitric acid. Fluorescence in lanes 2 5 was not detectable by naked eye.
Figure 4B:
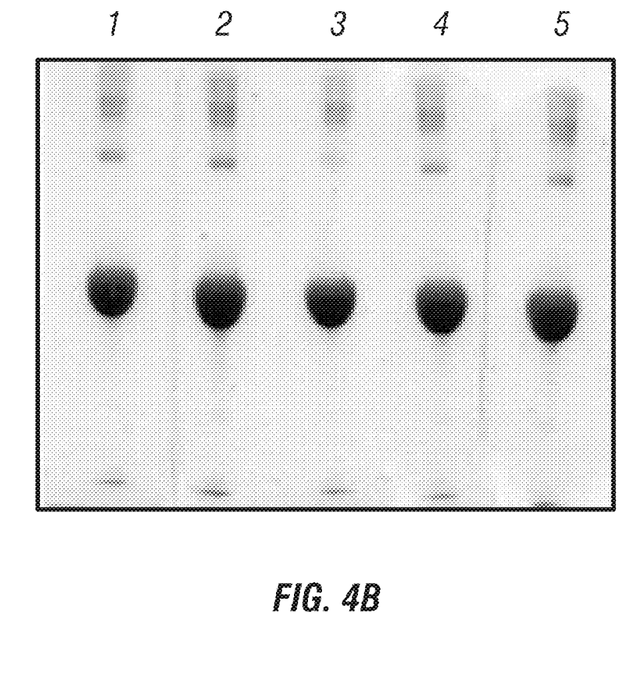

The applicants tested different acids to check whether this effect is solely pH dependent or if it is mediated by a chemical reaction with TCA. As shown in FIG. 4, a TCA soak produced bright visible fluorescence, while exposure of gels to other acids resulted in a dim glow, not visible by the naked eye against the UV background. Black and white photography, however, was able to record this weak fluorescence. The possibility that the observed fluorescence is caused by heat from the transilluminator rather than UV irradiation was eliminated by performed experiments in which fluorescence was developed using a hand-held UV lamp (data not shown). Also, band patterns could be recorded with a portable UV box positioned to the side of the gel, rather than immediately beneath it. In both cases heat transfer from the UV source to the gel was minimal.

The applicant further determined that heating of TCA-soaked gels: in the absence of UV exposure does not produce visible band pattern (data not shown). In addition, fluorescence spectra shown in FIGS. 5 and 6 were obtained in a temperature-controlled environment at 20° C. Taken together, these data suggest that the observed fluorescence of separated proteins is caused by UV illumination and is not induced by heating of the gel. The fluorescence observed after TCA or chloroform treatment of the gels can be explained in terms of fluorescent properties of products of a light-driven reaction of tryptophan with the trichlorocompound.

Figure 5:
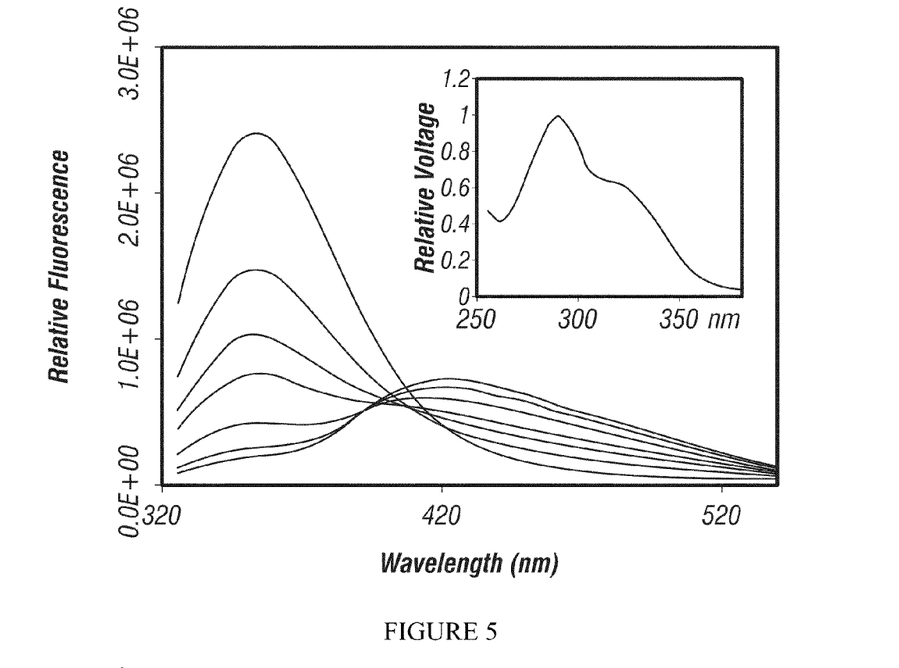
Figure 6:
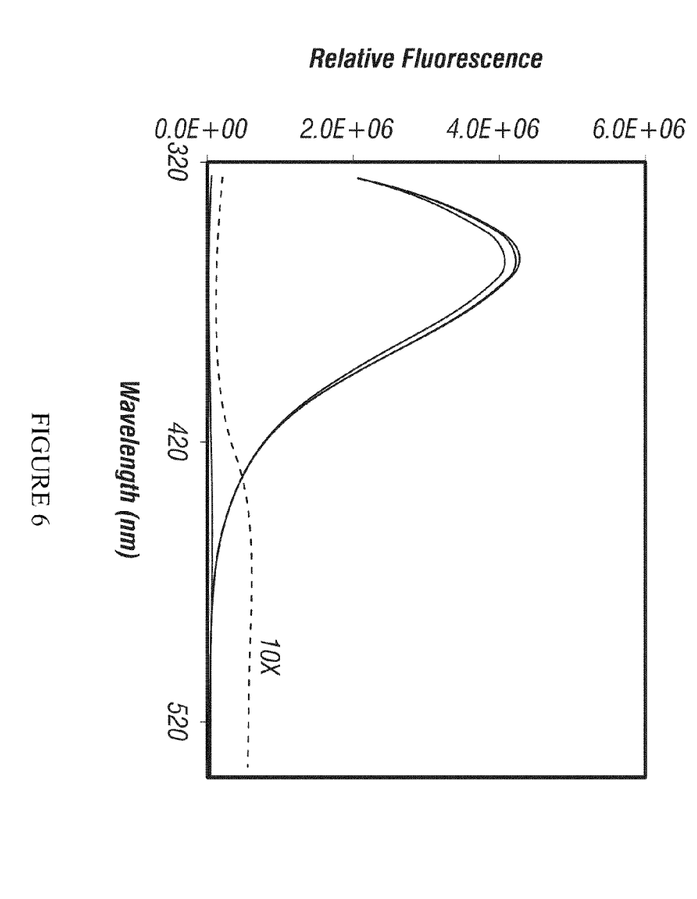

The fluorescence of tryptophan at 350 nm in aqueous solution is not visible. However, Vorobei et al. have shown that tryptophan undergoes a light-driven reaction with chloroform to yield products that emit in the visible part of the spectrum (9, 10). They also used 14C-labeled chloroform to show that the chloroform carbon is covalently attached to the tryptophan (10) in the products of this reaction. Recent 1H NMR evidence has established unequivocally that the chloroform hydrogen is also covalently attached and implies that the products of the reaction contain a $CHCl_2$ attached to the indole ring (11). FIG. 5 shows that tryptophan illuminated with UV light at 280 nm in the presence of trichloroacetic acid leads to a decrease in the indole fluorescence at 360 nm and the production of an emission band at approximately 420 nm. Similar experiments in which chloroform and N-acetyl-L-tryptophanamide (NAWA) or Trp are illuminated also show a decrease of the indole fluorescence and increase in long wavelength emission (23). Although the emission peak of the products of the light-dependent reaction of TCA and Trp is barely in the visible range at 420 nm, the long wavelength side of the band gives sufficient light to be observed with the naked eye. The environment of the SDS/protein/gel matrix may also give a red shift to make even more of this band visible. With chloroform, the emission peak produced is at somewhat longer wavelengths at about 480 nm, which is easily visible to the naked eye.

The excitation spectra in the inset of FIG. 5 for the products of the reaction between tryptophan and trichloroacetic acid shows a peak at about 290 nm with a shoulder at about 320 nm. The UV light produced in the transilluminator, which is primarily above 300 nm, would effectively excite via the 320-nm shoulder on the long wavelength side of the 290-nm peak. The fact that the fluorescence observed on the gels appears gradually over the course of UV irradiation supports the involvement of the UV-light-driven reaction between proteins embedded in the gel matrix and TCA. The asymmetry of the long-wavelength emission band indicates that multiple products are formed by the lightdriven reaction of Trp in TCA. The lack of an isobestic point near 400 nm also implies that a product initially is formed that undergoes further reactions. Although these products probably include the known weakly fluorescent degradation products of tryptophan: kynurenine, N-formyl kynurenine, and, with lesser yield, hydroxykynurenine (2428), there are new products formed in the presence of trichloro compounds in which the indole ring has been derivatized that have more intense emission in the visible region (9-11).

Figure 3C:
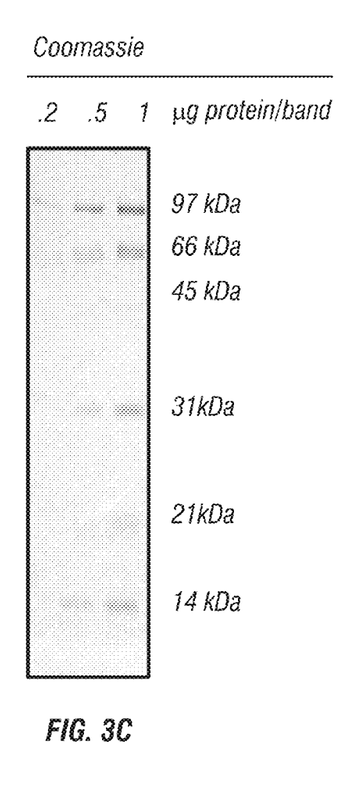

Further confirmation that the species that we are able to visualize is a tryptophan product can be found in FIGS. 1 and 3. We used low-molecular-weight markers from Bio-Rad (La Jolla, Calif.). In FIG. 1 the molecular weights of resolved protein markers are 97, 66, 45, 31, and 21 kDa, whereas the 12% gel in FIG. 3 also resolves the 14-kDa protein marker. As seen on CBB-stained gels (FIGS. 1B and 3C), mass load of 97-, 66-, and 31-kDa markers is approximately the same. However, the 31-kDa marker shows best on the UV-visualized gel (FIGS. 1A, 3A, and 3B), with 97 kDa following and 66-kDa marker almost invisible. This order of fluorescence intensity for the protein markers matches the tryptophan contents of the respective proteins. Bovine carbonic anhydrase (31.0 kDa) contains 4.5% Trp by weight, rabbit muscle phosphorylase B (97 kDa) contains 2.3% Trp, while BSA (66 kDa) contains only 0.8% Trp. The ovalbumin (45 kDa) band is always more diffuse and fainter than the other bands and has only 1.3% Trp. Trypsin inhibitor (22 kDa) with 1.8% Trp has a low mass load but a reasonably intense fluorescent band in FIGS. 3A and 3B. Lysozyme (14 kDa), with 7.8% Trp, has the most intense fluorescence band in FIG. 3 even though it is less intense on the CBB-stained gel (FIG. 3C).

We were able to document weak fluorescence of proteins after UV illumination with sulfuric, nitric, hydrochloric, and acetic acids. However, this fluorescence is too weak to be useful for visual protein detection. If Trp in HCl is illuminated in the fluorometer (FIG. 6) the decrease in indole fluorescence is much slower than was the case for TCA and no long-wavelength emission is observed. However, when NAWA in HCl is illuminated, a very weak broad long-wavelength emission band is observed (shown at 10-fold magnification in FIG. 6) from a reaction which must involve the amide part of the NAWA since it is not observed with Trp. This is consistent with the results of Holt et al., (14), who concluded that the light-dependent degradation of Trp containing peptides leads to significant amounts of products with higher molecular weight than the reacting peptide due to crosslinking.

Example 3

Pre-Electrophoretic Incorporation of Trichloroethanol (TCE)

Low molecular weight standards, 1.5, 3.0, 6.0, and 9.0 µg per lane which corresponds to 0.25, 0.5, 1.0, and 1.5 µg per band, were separated on a 12% SDS-PAGE gel Protean II gel system (Bio-Rad Laboratories, Hercules, Calif., USA) as per the standard Laemmli method (17). Low-molecular-weight standards were from Bio-Rad Laboratories. They contained phosphorylase b (97 kDa, 2.3% Trp), serum albumin (66 kDa, 0.8% Trp), ovalbumin (45 kDa, 1.3% Trp), carbonic anhydrase (31 kDa, 4.5% Trp), trypsin inhibitor (21 kDa, 1.8% Trp), and lysozyme (14 kDa, 7.85 Trp). All tryptophan percentages are calculated as percentage weight. Other purified protein samples loaded were EmrE, DmsD:His6, and TehB:His6. EmrE was purified according to Winstone et al. (18). DmsD:His6 (19) and TehB:His6 (20) were purified with a nickel agarose column followed by size exclusion chromatography. For CBB method the gel was then stained in Coomassie brilliant blue dye overnight, followed by 5 hours destaining. For the TCE in gel method, 0.5% vol/vol TCE (Sigma) was dissolved in the buffer and then acrylamide, SDS, ammonium persulphate and TEMED were added to polymerize the separating gel. The stacking gel is prepared as usual.

Proteins were visualized by placing the gel on a UV transilluminator and irradiating the gel for 2 to 5 minutes, during which time the protein bands become visible as bluish-green bands against a pale blue background of the gel matrix. An UltraLum™ Electronic UV transilluminator (300 nm) with COHU™ High Performance Monochrome CCD Camera (Rose Scientific), was used to take photographs of the gel. Pixel intensity in bands was determined using Scion Image V1.62 software (ftp: zippy.nimh.nih.gov). The density of the background above and below a band is averaged and the density of the band is subtracted from this giving the intensity of the band.

It is apparent that visualization with TCE-ultraviolet light modified tryptophan is in some cases more sensitive than CBB and faster. FIGS. 7A and 7B shows 12% SDS-PAGE gels loaded with low molecular weight standards detected with 0.5% TCE in the gel and with CBB staining. Comparison of panel A with B shows that TCE is more sensitive than CBB staining. The sensitivity limit of CBB is sensitive in the sub µg range and the limit changes for different proteins (21). The presence of TCE in gels during electrophoresis does not appear to impair the mobility of the proteins because adding TCE to the gel before electrophoresis does not shift the protein bands (results not shown). All of the protein bands are clearly visible when only 0.25 µg per band of standards are loaded in a 0.5% (v/v) TCE gel. An alternative method is to soak the gel post-electrophoresis with 10% TCE. In this case the bands are almost as intense (results not shown) as when TCE was put into the gel, but adding TCE to the gel during polymerization significantly decreases the processing time.

Figure 1A:
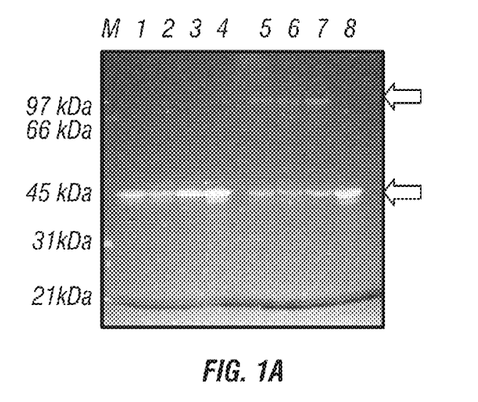
FIG. 1A shows a recombinant protein (lanes 1 and 5) and three of its mutants (Mutant 1, lanes 2 and 6; Mutant 2, lanes 3 and 7; Mutant 3, lanes 4 and 8) were resolved on SDSPAGE. Samples in lanes 14 were treated with β-mercaptoethanol prior to loading on the gel. The proteins in the gel were visualized by soaking the gel in trichloroacetic acid (TCA) post electrophoresis followed by ultraviolet (UV) transillumination.
Figure 1B:
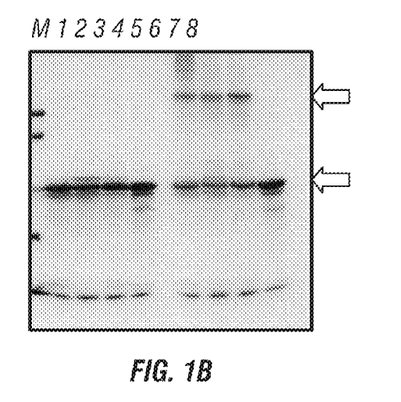
FIG. 1B shows the same gel stained overnight with Coomassie brilliant blue (CBB) R-250. Monomeric recombinant protein is indicated by a filled arrow. Predominant oligomer is indicated by an open arrow.
Figure 1C:
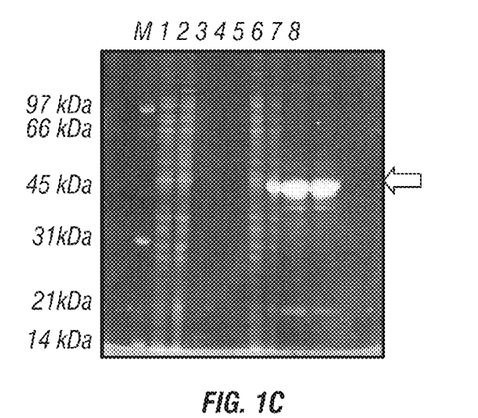
FIGS. 1C (TCA) and 1D (CBB) show the results of two *Escherichia coli* clones tested for expression of a recombinant protein. Lanes 14, clone 1; lanes 58, clone 2. Lanes 1 and 5, total bacterial protein prior to induction; lanes 2 and 6; total bacterial protein after induction; lanes 3, 4, 7, and 8, affinity-purified recombinant protein isolated by two slightly varying protocols. Recombinant protein is indicated by a filled arrow. M—molecular weight markers.
Figure 1D:
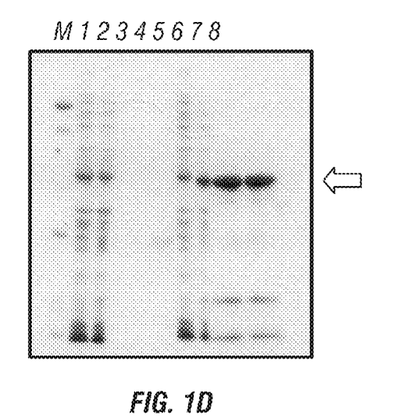

Haloalkane-UV modified tryptophans visualization may be especially useful for membrane proteins. DmsD (19) (8.7% Trp), a peripheral membrane protein, contains 8.7% percent tryptophans and is visualized with TCE better than CBB as shown in FIG. 1B. TehB (20), a soluble protein, appears to be visualized with equal intensity by both methods. An integral membrane protein, EmrE (18) (5.0% Trp) at 0.5 µg, is not seen when stained with CBB as shown in FIG. 1C. In comparison the TCE in gel technique gives very intense bands at just 0.25 µg as shown in FIG. 1C.

Example 4

Pre-Electrophoretic Incorporation: Optimization and Sensitivity

In optimization studies 0.02, 0.05, 0.1, 0.2, 0.5, 1.0 and 2.0% TCE (vol/vol) were added to the gel before polymerization. For the TCE staining the 12% SDS-PAGE was run and then soaked in 10% TCE (v/v) in water:methanol (1:1) for ten minutes. Then the gel was washed in water and visualized as described above.

Calculating the intensities for FIGS. 2 and 3A, the sum of the intensity of phosphorylase b, albumin, ovalbumin and trypsin bands was used. These were chosen because they contain percentages of tryptophan near the average for soluble proteins. Four sets of 0.25 µg and 0.5 µg bands were used to calculate intensity per µg.

Figure 8:
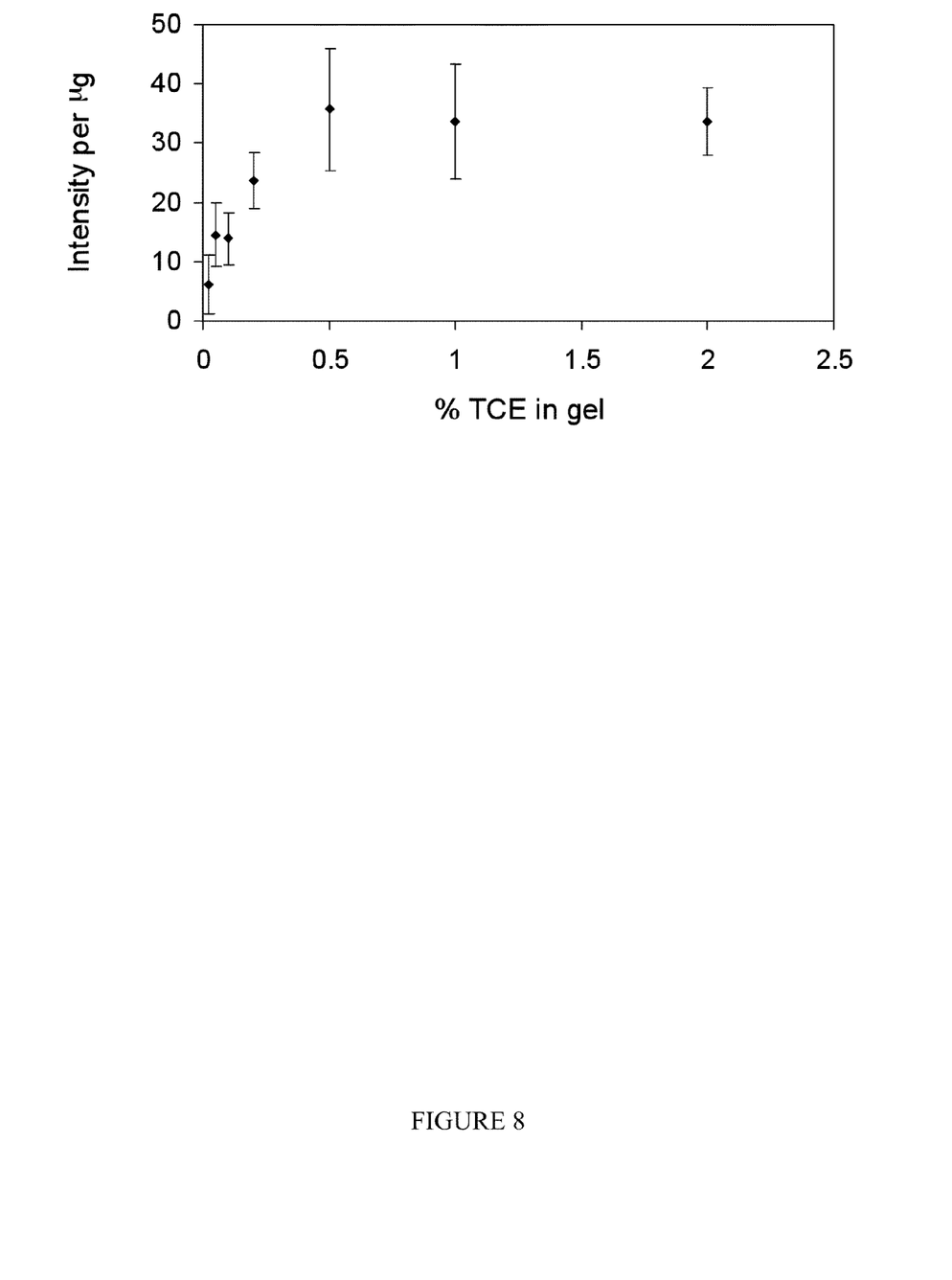

FIG. 8 shows that maximum intensity is reached with a TCE concentration of 0.5% and that lower concentrations have a lower intensity while higher concentrations do not have higher intensities.

FIG. 3A shows that intensity increases nearly linearly with the amount of protein up to about 2 µg per band. FIG. 3B shows that increasing Trp content in the protein correlates with higher intensities per µg of protein.

Example 3

Western Blots after Fluorescent Visualization

In addition to rapid protein detection, the methods described herein allows for visualization of proteins before western blotting. FIG. 7C shows proteins visualized by TCE in gel followed by a western blot. This will allow for confirmation that an appropriate protein pattern is seen before performing a western blot procedure. In addition this demonstrates that TCE in the gel does not hinder transfer of proteins to nitrocellulose.

For the western blot shown in FIG. 7C, immediately after visualizing 12% SDS-PAGE with 0.5% TCE, the gel was electroblotted to nitrocellulose (TransBlot). The blot was then blocked overnight with 5% milk in Tris Buffer Saline. The blot was then incubated with the primary antibody, anti-His6 (Cedarlane Laboratories Ltd, Hornby, ON, CAN), washed and incubated with goat antimouse horseradish peroxidase: conjugate and detected with the HRP conjugate substrate kit (Bio-Rad Laboratories). All protein bands visualized under UV light were detected after blotting to nitrocellulose.

References The following references are incorporated herein by reference as if reproduced in their entirety.
1. Ristow, S. S., Starkey, J. R., Stanford, D. R., Davis, W. C., and Brooks, C. G. (1985) Cell surface thiols, but not intracellular glutathione, are essential for cytolysis by a cloned murine natural killer cell line. *Immun. Invest.* 74, 401-414
2. Hartman, B. K., and Udenfriend, S. (1969) A method for immediate visualization of proteins in acrylamide gels and its use for preparation of antibodies to enzymes. *Anat. Biochem.* 30, 391-394
3. Andrews, A. T. (1981) Electrophoresis: theory, techniques and biochemical and clinical applications. Oxford University Press, New York.
4. Dunn, M. J. (1993) Gel Electrophoresis: Proteins. Bios Scientific Publishers Ltd. Oxford, Great Britain.
5. Steinberg, T. H., Jones, L. J., Haugland, R. P., and Singer, V. L. (199.6) SYPRO orange and SYPRO red protein gel stains: One-step fluorescent staining of denaturing gels for detection of nanogram levels of protein. *Anal. Biochem.* 239, 223-237.
6. Berggren, K., Chemokalskaya, E., Steinberg, T. H., Kemper, C., Lopez, M. F., Diwu, Z., Haugland, R. P., Patton, W. F. Background-free, high sensitivity staining of proteins in one- and two-dimensional sodium dodecyl sulfate-polyacrylamide gels using a luminescent ruthenium complex. *Electrophoresis* 21, 2509-2521 (2000).
7. Jones, D., T., Taylor, W. R., and J. M. Thornton. A mutation data matrix for transmembrane proteins. *FEBS letters* 339, 269-275 (1994).
8. Deber, C. M., Brandi, C. J., Deber, R. B., Hsu, L. c. and X. K. Young. Amino acid composition of the membrane and aqueous domains of integral membrane proteins. 1986 257, 68-76 (1986).
9. Voropei, A. V., Chemitskii, Ye. A., Konev, S. V., Krivitskii, A. P., Pinchuk, S. V., and Shchukanova, N. A. (1992) Chloroform-Dependent photoproducts of tryptophan. *Biophysics* 37, 743-745.
10. Pinchuk, S. V., and Vorobei A. V (1993) Spectral characteristics of mechanisms of forming "chloroform-dependent" tryptophan photoproducts. *J. Appl. Spectrosc.* 59, 711-715
11. Edwards R. A., Jickling, G., and Turner, R. J. (2001) The light dependent reaction between chloroform and tryptophan. *Proceedings of the 45th annual meeting of the Biophysical Society.* p. 364a.
12. Asquith, R. S., and Rivett, D. E. (1971) Studies on the photooxidation of tryptophan. *Biochim. Biophys. Acta* 252, 111-116
13. Finley, E. L., Dillon, J., Crouch, R. K., and Schey, K. L. (1998) Identification of tryptophan oxidation products in bovine alpha-crystallin. *Prot. Sci.* 7, 2391-2397
14. Holt, L. A., Milligan, B., Rivett, D. E. and Stewart, F. H. H. (1977) The photodecomposition of tryptophan peptides. *Biochim. Biophys. Acta* 499, 131-138
15. Sen, A. C., Ueno, N., and Chakrabarti, B. (1992) Studies on human lens: I. Origin and development of fluorescent pigments. *Photochem. Photobiol.* 55, 753-764
16. Creed, D. (1984) The photophysics and photochemsitry of the near-UV absorbing amino acids-I. Tryptophan and its simple derivatives. *Photochem. Photobiol.* 39, 537-562.
17. Laemmli, U. K. *Nature* 227, 680-685 (1970)
18. Winstone, T. L., Duncalf, K. A, and R. J. Turner. Optimization of expression and the purification by organic extraction of the integral membrane protein EmrE. *Protein Expression and Purification* 26, 111-121 (2002).
19. Oresnik, I. J., Ladner, C. L. and Rj. Turner. Identification of a twin-arginine leader-binding protein. *Molecular Microbiology* 40, 323-331 (2001).
20. Liu, M., Turner, R. J., Winstone, T. L., Saetre, A., Dyllick-Brenzinger, M., tickling, G., Tari, L. W., Weiner, J. H. and D. E. Taylor. *Escherichia coli* TehB Requires S-Adenosylmethionineas as a Cofactor to Mediate Tellurite Resistance. *Journal of Bacteriology* 182, 6509-6513 (2000).

21. Patton, W. F. A thousand points of light: The application of fluorescence detection technologies two-dimensional gel-electrophoresis and proteomics. *Electrophoresis* 21, 1123-1144 (2000).

The invention claimed is:

1. A method of detecting proteins in a polyacrylamide gel, comprising the steps of:
   (a) incorporating an aliphatic hydrocarbon substituted with at least one halogen atom into the gel pre-electrophoresis, which aliphatic hydrocarbon substituted with at least one halogen atom reacts with tryptophan residues in proteins added to the gel to form fluorescent compounds when illuminated with ultraviolet light;
   (b) electrophoretically separating the proteins in the gel;
   (c) illuminating the gel with ultraviolet light; and
   (d) detecting the fluorescence of the formed compounds.

2. The method of claim 1 wherein the aliphatic hydrocarbon substituted with at least one halogen atom is a trichloroalkane.

3. The method of claim 2 wherein the trichloroalkane is selected from the group consisting of chloroform, trichloroacetic acid and trichloroethanol, or mixtures thereof.

4. The method of claim 1 wherein the gel comprises between about 0.02% to about 2.0% trichloroalkane (v:v) added prior to polymerization of the gel.

5. The method of claim 4 wherein the gel comprises between about 0.10% to about 1.0% trichloroalkane (v:v) added prior to polymerization of the gel.

6. The method of claim 5 wherein the gel comprises about 0.5% trichloroalkane (v:v) added prior to polymerization of the gel.

7. A polyacrylamide gel for electrophoretically separating proteins by molecular weight, the gel comprising an aliphatic hydrocarbon substituted with at least one halogen atom which reacts with tryptophan residues in the proteins to form compounds which fluoresce when subjected to ultraviolet light, wherein said gel does not contain protein nor is it immersed in buffer.

8. The polyacrylamide gel of claim 7 wherein the aliphatic hydrocarbon substituted with at least one halogen atom is selected from the group consisting of chloroform, trichloroacetic acid, and trichloroethanol, or mixtures thereof.

9. A method of forming a polyacrylamide gel for electrophoretically separating proteins by molecular weight, comprising the step of incorporating into the gel an aliphatic hydrocarbon substituted with at least one halogen atom which reacts with tryptophan residues in the proteins to form compounds which fluoresce when subjected to ultraviolet light, wherein the aliphatic hydrocarbon substituted with at least one halogen atom is incorporated into the gel prior to polymerization of the gel.

10. The method of claim 9 wherein the aliphatic hydrocarbon substituted with at least one halogen atom is selected from the group consisting of chloroform, trichloroacetic acid, and trichloroethanol, or mixtures thereof.

* * * * *